United States Patent [19]
Zadeh et al.

[11] Patent Number: 5,573,550
[45] Date of Patent: Nov. 12, 1996

[54] IMPLANTABLE STIMULATION DEVICE HAVING A LOW NOISE, LOW POWER, PRECISION AMPLIFIER FOR AMPLIFYING CARDIAC SIGNALS

[75] Inventors: Ali E. Zadeh, Sierra Madre; Wayne A. Morgan, Granada Hills, both of Calif.

[73] Assignee: Pacesetter, Inc., Sylmar, Calif.

[21] Appl. No.: 431,363

[22] Filed: Apr. 28, 1995

[51] Int. Cl.$^6$ ............................................. A61N 1/00
[52] U.S. Cl. .................................................. 607/28
[58] Field of Search ................................. 607/9, 28, 29

[56] References Cited

U.S. PATENT DOCUMENTS 5,330,512  7/1994  Hauck et al. .................... 607/28
5,443,485  8/1995  Housworth et al. .............. 607/28

Primary Examiner—William E. Kamm
Assistant Examiner—Scott M. Getzow
Attorney, Agent, or Firm—Lisa P. Weinberg

[57] ABSTRACT

An implantable stimulation device has a sensing amplifier circuit for amplifying low amplitude cardiac signals, while maintaining low power, to produce an output signal having a low noise level. The sense amplifier circuit includes a two-stage amplifier, a bandpass filter, and a threshold detector. The first stage comprises a linear differential amplifier which has low gain, good common mode rejection, and a current consumption proportional to the gain. The second stage is a switched-capacitor amplifier which has a programmable gain and low current consumption. The noise content of the system is low and produced substantially entirely in the switched-capacitor amplifier.

22 Claims, 3 Drawing Sheets

IMPLANTABLE STIMULATION DEVICE HAVING A LOW NOISE, LOW POWER, PRECISION AMPLIFIER FOR AMPLIFYING CARDIAC SIGNALS

FIELD OF THE INVENTION

The present invention relates to implantable medical devices and more particularly to a low power, low noise precision amplifier suitable for use in implantable medical devices, such as pacemakers, cardioverters and defibrillators, etc.

BACKGROUND OF THE INVENTION

An implanted cardiac pacemaker is coupled to one or two implantable stimulation leads which are implanted in one or both chambers of a patient's heart, respectively. Physical contractions of the heart muscle tissue generate low amplitude electrical signals (e.g., P-waves or R-waves) which can be monitored to obtain indications of the physical condition of the heart, and in particular to provide a basis for determining whether stimulation pulses must be supplied to the heart from the pacemaker. The implantable stimulation leads may be either unipolar, having a single tip electrode at the distal end of the lead, or bipolar, having a tip and ring electrode at the distal end of the lead. In the unipolar configuration, the pacemaker case acts like the return electrode. Thus, the stimulation pulses may be delivered either tip-to-case (unipolar) or tip-to-ring (bipolar).

A sensing module is typically coupled to the electrodes and is programmable between unipolar sensing and bipolar sensing modes. A pulse generator generates electrical stimulation pulses as a function of the status of cardiac signals supplied to the sensing module.

Proper sensing of low level intracardiac signals (e.g., P. waves and R-waves) depends on the fidelity, and accuracy, with which the these low level signals are amplified. In addition, implantable medical devices, such as cardiac pacemakers, operate with a self-contained power source that must have a long useful life, primarily when replacement of the power source requires a surgical procedure.

Proposals to satisfy these diverse, and somewhat contradictory, requirements have involved a wide variety of amplifier types. In particular, amplifiers of the continuous, linear type offer excellent signal amplification quality at the price of relatively high current consumption. On the other hand, a class of amplifiers typified by switched-capacitor amplifiers offer relatively low current consumption but introduces a significant noise component into the amplified signal, this noise component being due essentially to the turning off of switches associated with the capacitors. It therefore follows that each of these amplifiers has shortcomings with respect to one system requirement or another.

SUMMARY OF THE INVENTION

The disadvantages and limitations of the background art discussed above are overcome by the present invention. The present invention provides an implantable cardiac pacemaker having an improved sense amplifier circuit for amplifying a low amplitude cardiac signals, while maintaining low current consumption, to produce a precision output signal having low noise.

More particularly, the present invention comprises a sensing module which has a two-stage amplifier, including a linear first-stage amplifier and a switch-capacitor second-stage-amplifier. The output of the second-stage is typically coupled to a bandpass filter circuit before it reaches a threshold detector, or comparator. Both the gain and the threshold of the comparator may be programmably adjusted so that the absence or presence of low level signals (e.g., P-waves and R-waves) may be detected.

The first-stage amplifier includes a linear amplifier having a first gain and a current consumption proportional to the first gain. The first-stage amplifier includes a differential input connected to receive the input signal and a differential output for providing an intermediate signal which is an amplified version of the input signal with a low noise content. In one embodiment, the gain of the first-stage amplifier could be programmable, however, to keep the current drain low, the gain should be kept relatively low (e.g., a gain of 10).

The second-stage amplifier constitutes a switched-capacitor amplifier having a second gain and a very low current consumption. The second-stage amplifier has a differential input connected to the first-stage amplifier differential output to receive the intermediate output signal. The two-stage amplifier has a single-ended output which provides an output signal having a noise content produced substantially entirely in the second-stage amplifier. Advantageously, the noise content of this two stage amplifier primarily comes from its second stage, the switched-capacitor amplifier, since the first stage does not have any switching noise. Because the input signal has been amplified by the first stage, the switching noise of the second stage will not be as significant compared to a single, stand-alone switched-capacitor amplifier.

In the preferred embodiment, optimum performance of the sense amplifier is achieved by matching the aspect ratios (i.e. the ratio of channel width to channel length) of the various FETs. Consequently, the sense amplifier will not be dependent on process variations, the individual on-chip resistors, or temperature. The gain will only depend on the ratio of on-chip resistors, on-chip capacitors, and the aspect ratios of the associated FETs. Therefore, the accuracy of the amplification produced by the sense amplifier circuit will be within 1 to 2%.

It is a feature of the present invention to provide a sense amplifier circuit which produces a satisfactory amplified version of a low level input signal while having a low average current consumption to promote prolonged battery life.

Another feature of the invention is to provide a sense amplifier circuit which provides an output signal having an acceptably low noise level.

Still another feature of the invention is to provide improved performance with an amplifier formed as an IC circuit of compact size.

BRIEF DESCRIPTION OF THE DRAWINGS

The above and further features, advantages and benefits of the present invention will be apparent upon consideration of the following detailed description, taken in conjunction with the accompanying drawings, in which like reference characters refer to like parts throughout, and in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims.

Figure 1:
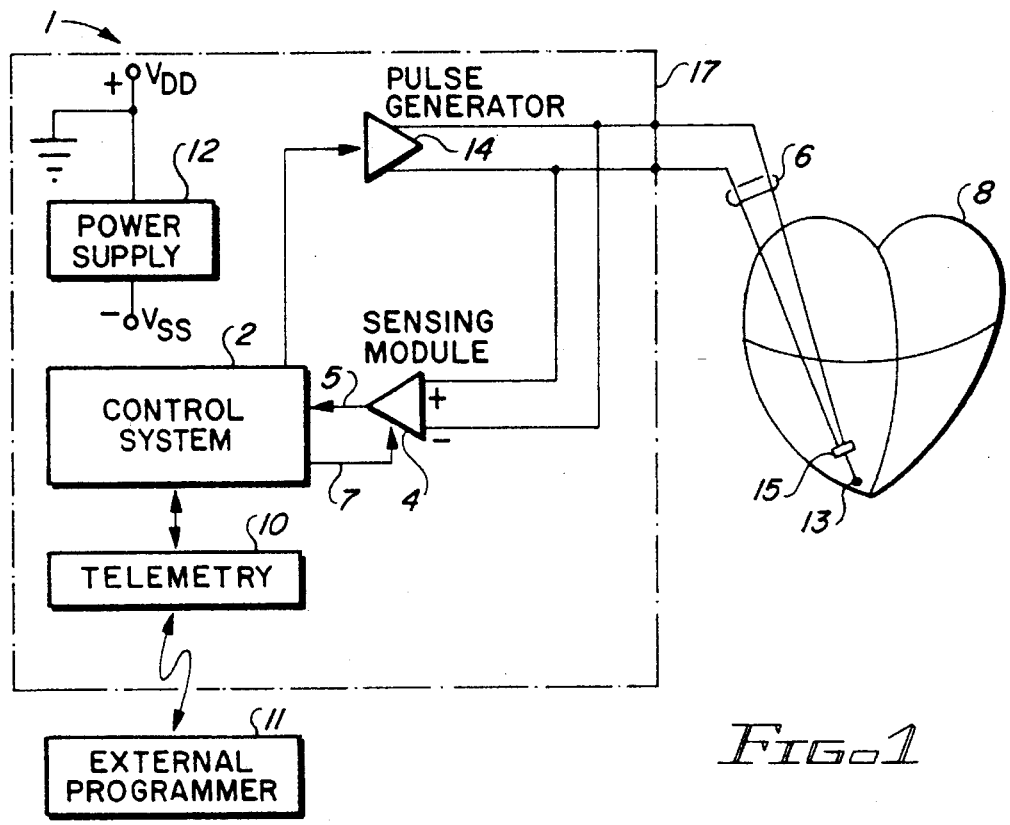
FIG. 1 is a block diagram showing a pacemaker which can be constructed according to the invention, having a stimulation lead implanted in a patient's heart.

FIG. 1 is a block diagram showing the basic arrangement of an exemplary implantable pacemaker 1 of the type currently in use. While the present invention is presented in terms of a single-chambered implantable pacemaker, it is understood that it could also be implemented in a cardioverter/defibrillator device or antitachycardia device, and that one skilled in the art could easily adapt the present invention for dual chamber sensing.

The basic components of such a pacemaker 1 include a control system 2 (e.g., a microprocessor, a state machine or other processing system, a memory and/or digital control logic (not shown)), a sensing module 4, and a pulse generator 14. The control system 2 triggers the pulse generator 14 to generate stimulation pulses to a stimulation lead 6, as needed, at the appropriate timing intervals and output level. The sensing module 4 senses cardiac signals from the stimulation lead 6 and provides this information to the control system 2 so that stimulation pulses may be inhibited in the presence of cardiac signals. The control system 2 also controls the gain, or sensitivity, of the sensing module via a signal appearing on line 7. A power source 12 supplies operating power to all the electronic components of the pacemaker 1.

A telemetry module 10, connected to the control system 2, includes conventional means for exchanging telemetry communication signals with an external programmer 11. The pacemaker 1 can be adjusted after implantation by these telemetry communication signals originating from outside of the patient's body and received by the telemetry module 10. In this way, programming instructions and data are transmitted to and from the control system 2.

As shown in FIG. 1, the lead 6 is a bipolar lead having a tip electrode 13 and a ring electrode 15, which are implanted in the heart 8. While the electrodes 13 and 15 are shown located in the ventricle, the lead 6 may be coupled to the atrium or ventricle, or include a second lead for coupling both chambers of the heart. Furthermore, while a bipolar lead 6 is depicted in FIG. 1, it is also known in the art to use a case electrode 17 and the tip electrode 13 in a unipolar fashion, i.e., for sensing tip-to-case. For a unipolar configuration, the sensing module 4 would include appropriate switches to programmably select either the case electrode 17 or the ring electrode 15 as the return electrode.

The requirements for the sensing module 4 may be best understood through a description of the sensing requirements for the implantable pacemaker of the prior art. The sensing module 4 must amplify intrinsic heart electrical signals which consist of signals having amplitudes of the order of 0.1 to 10 mV, to enable those signals to be processed and detected with sufficient accuracy. In addition, the sensing module 4 must filter the input signals to eliminate noise and other unwanted signal components that may be present. The front-end amplifier of the sensing module 4 typically must be a low noise, precision amplifier having a programmable gain and constructed to amplify incoming low level signals with high accuracy.

A typical embodiment of the sensing module of the prior art would be composed of a series arrangement of a single, front-end amplifier, including bandpass filter circuitry, coupled to comparator, or threshold detector. The front-end amplifier is coupled to the selected electrodes (e.g., tip and ring electrodes or tip and case electrodes) to receive low amplitude cardiac signals.

In order for a sensing module to be able to produce signals having useful amplitudes, the gain of the front-end amplifier must be relatively high. In order to prevent sensing of stimulation pulses, the inputs of sensing module are decoupled, or blanked, from the electrodes when stimulation pulses are being produced by the pulse generator. The inputs of the sensing module are then coupled to the electrodes after a prescribed blanking interval is over. At this time, a large residual polarization voltage from the stimulation pulse may still be present on the electrodes.

An advantage of bipolar sensing is the use of differential sense amplifiers as the front-end amplifier which eliminates the common mode voltage seen by both the tip electrode and the ring electrode. The low level signals produced by heart muscle contractions (i.e., P-waves or R-waves) appear as a differential voltage between the tip electrode and the ring electrode, with a large portion of the common-mode residual voltage signal being rejected by the differential sense amplifier. However, additional charge reduction circuitry (not shown) may still be required to reduce the residual polarization. This charge reduction circuitry is typically included in the pulse generator 14 and is well known in the art.

Thus, an advantage of using differential sense amplifiers within the sensing module of the prior art is to reject the common-mode residual voltage signal and to amplify the differential signal to a usable value while, as noted above, filtering out unwanted spurious signals and providing an output signal which allows accurate detection of the incoming P-waves or R-waves.

According to the present invention, the sensing module 4 is provided with a novel front-end amplifier which has the following, previously unattainable, combination of operating characteristics: very low noise; very high precision; and very low current consumption. In addition, the front-end amplifier according to the invention can be manufactured by CMOS technology, has a programmable gain capability, and has a very high common mode rejection capability to attenuate the large common mode residual voltage signal resulting from stimulation pulses.

The front-end amplifier will receive a differential signal having a level of between 0.1 mV and 10 mV and is to produce an output having a level on the order of 10 mV. Therefore, the desirable gain of the front-end amplifier is between 1 and 100.

As will be discussed in greater detail below, in comparison with conventional front-end amplifiers (which consist of either a single, linear amplifier or a single, switched-capacitor amplifier), the present invention achieves the above-discussed improvements by constituting the front-end amplifier of a cascaded arrangement of a linear, fully differential amplifier followed by a switched-capacitor amplifier.

Figure 2:
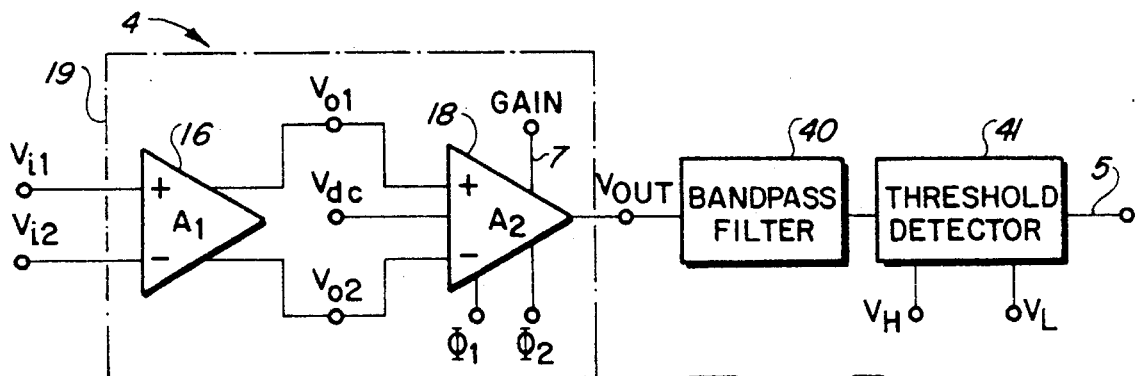
FIG. 2 is a circuit diagram of a sensing module according to the present invention.

In FIG. 2, the basic structure of the sensing module 4, according to the present invention, is shown. The sensing module includes a front-end amplifier 19, a bandpass filter 40 and a threshold detector 41. The threshold detector 41 is preferably biphasic, that is, it compares the filtered input signal to a high reference voltage, $V_H$, and to a low reference voltage, $V_L$. The threshold detector 41 is of conventional construction well known to one skilled in the art.

The front-end amplifier 19 includes a linear, differential amplifier 16 having a gain $A_1$, serving as the first stage of the front-end amplifier 19, and a switched-capacitor amplifier 18 serving as the second stage. The differential amplifier 16 has two inputs connected to receive differential input signals, $V_{i1}$ and $V_{i2}$, respectively, corresponding to those appearing on the electrodes (e.g., tip electrode 13 and ring electrode 15).

In the preferred embodiment, the differential amplifier 16 has two differential output leads on which appear signals $V_{o1}$ and $V_{o2}$, constituting amplified versions of the input signals appearing on the electrodes. The output signals from the differential amplifier 16 are applied to the differential inputs of a switched-capacitor amplifier 18, which has a gain $A_2$. It is within the spirit of the present invention to use a differential amplifier having a single-ended output coupled to a switched-capacitor amplifier in either an inverting or an non-inverting configuration. However, the advantage of the differential output is that the input capacitors (not shown) for the switched-capacitor amplifier 18 can be made symmetric, or balanced, as will be seen in conjunction with the description of FIG. 4.

Figure 4:
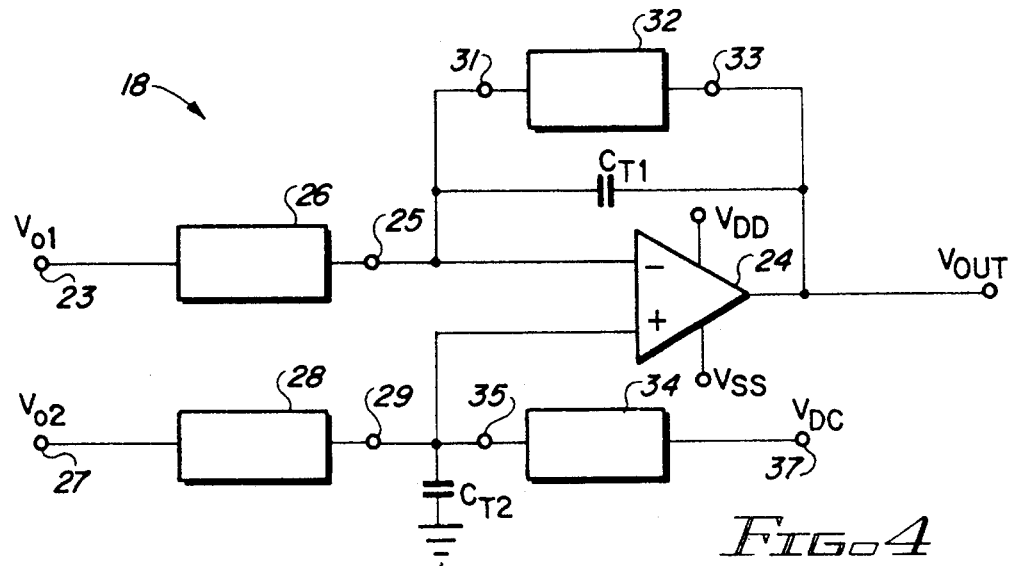
FIG. 4 is a circuit diagram of a preferred embodiment of the second stage amplifier (i.e., a switched-capacitor amplifier) of the sensing module of FIG. 2.

The switched-capacitor amplifier 18 also receives a DC input voltage, $V_{dc}$, for biasing the switched-capacitor amplifier 18 (described in conjunction with FIG. 4).

The switched-capacitor amplifier 18 produces an output voltage, $V_{out}$, relative to circuit ground, where:

$$V_{out} = A_1 A_2 (V_{i1} - V_{i2}).$$

Figure 7:
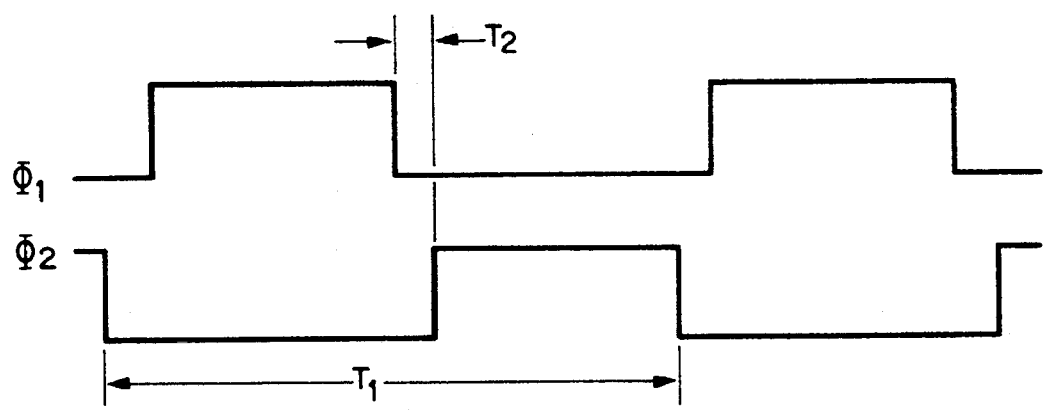
FIG. 7 is a timing diagram of two non-overlapping clock signals used for the second stage amplifier.

Since the second stage is a switched-capacitor amplifier, its operation requires the delivery of two non-overlapping clock signals having phases $\phi_1$ and $\phi_2$, as shown in FIG. 7. Typically, the period, $T_1$, of the clock signal is equal to 1/(sampling frequency), and is much greater than the non-overlapping time period, $T_2$. The circuitry required to produce such non-overlapping signals is conventional and well known in art, therefore such circuitry will not be reproduced here.

In addition, the switched-capacitor amplifier 18 preferably has a programmable gain, via line 7, controlled by the application of gain selection voltages from the control system 2, as will be described in greater detail below.

Figure 3:
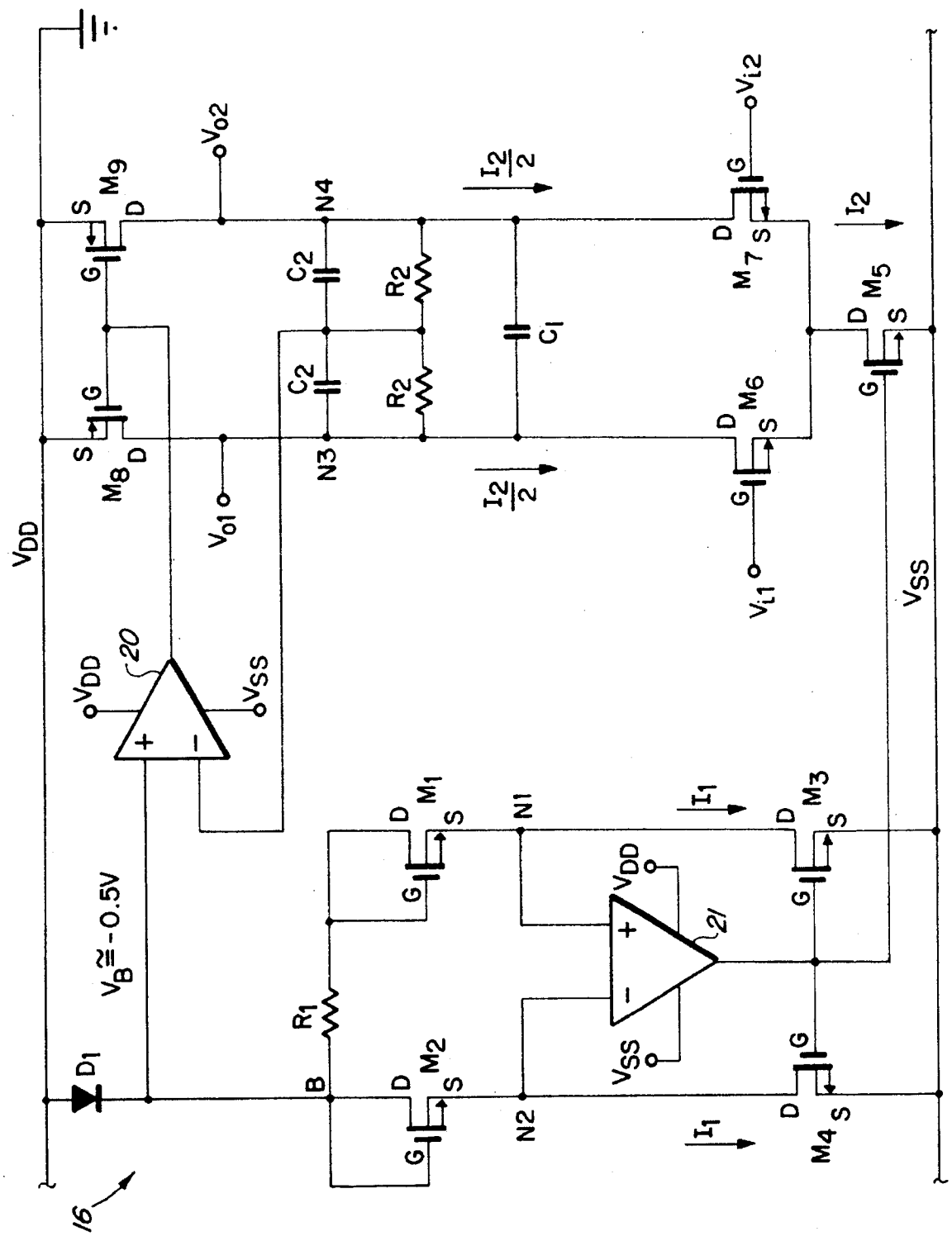
FIG. 3 is a circuit diagram of a preferred embodiment of the first stage amplifier of a sensing module of FIG. 2.

For the sake of completeness, exemplary embodiments of differential amplifier 16 and switched-capacitor amplifier 18 are shown in FIGS. 3 and 4, respectively. It is to be understood, however, that, although the specific amplifiers illustrated in those figures represent what are presently considered to be preferred embodiments thereof, many other embodiments are considered to be within the scope and spirit of the present invention.

In an exemplary pacemaker, $V_{DD}$ is the pacemaker ground potential and Vss equals $-2.8$ V when the pacemaker battery is fresh and equals $-1.8$ V at the end of the useful life of the pacemaker battery. The reason for this "pacing convention" is that stimulation pulses must be negative in order to stimulate the heart. This "pacing convention" will be used throughout the following description.

As shown in FIG. 3, the embodiment of the linear, differential amplifier 16, includes FETs $M_1$–$M_9$, all of which may be MOSFETs. The FETs $M_8$ and $M_9$ are PMOS devices, while all of the other FETs are NMOS devices. This embodiment further includes two operational amplifiers (op-amps) 20 and 21, resistors $R_1$ and $R_2$, capacitors $C_1$ and $C_2$ and a diode $D_1$.

Before describing the functionality of the FETs in the differential amplifier 16, it would be beneficial to first described their interconnection. As is well known in the art, each FET has a drain, a source, a gate, and a substrate which is (typically, and as shown in FIG. 3) connected to the source of the respective FET; each diode has an anode and a cathode; and each operational amplifier, powered between $V_{DD}$ and $V_{SS}$, has an inverting input (–), a non-inverting input (+) and an output. For the sake of clarity, numeric designators for each of these inherent parts of the elements have been omitted, and alphanumerics ($M_1$, $C_1$, $R_1$, etc.) will be used for the elements, since one skilled in the art would be able to construct the present invention based on the technical description provided below when taken in conjunction with the figures.

A diode $D_1$ has its anode connected to $V_{DD}$ (i.e., pacemaker ground potential) and its cathode connected at node B to the drain of a FET $M_2$, one end of a resistor, $R_1$, and to an inverting input of an operational amplifier (op-amp) 20. The other end of the resistor $R_1$ is, in turn, connected to the drain of a FET $M_1$. The FETs $M_1$ and $M_2$ have their gates connected to their respective drains and are, thus, configured as diode connected transistors. The sources of the FETs $M_1$ and $M_2$ are connected to nodes $N_1$ and $N_2$, respectively. FETs $M_3$ and $M_4$ have their drains connected to nodes $N_1$ and $N_2$, respectively, with their sources being connected to $V_{ss}$. An operational amplifier (op-amp) 21 has a non-inverting input connected to the node $N_1$, and an inverting input connected to the node $N_2$. The output of the op-amp 21 is connected to the gate electrodes of the FETs $M_3$, $M_4$ and also to a FET $M_5$.

FETs $M_8$ and $M_9$ have their sources connected to $V_{DD}$ and their drains connected to nodes $N_3$ and $N_4$, respectively. The output of op-amp 20 is connected to the gates of both the FETs $M_8$ and $M_9$.

A first differential output voltage, $V_{o1}$, of the differential amplifier 16 is taken from node $N_3$. A second differential output voltage, $V_{o2}$, is taken from node $N_4$.

Connected across nodes $N_3$ and $N_4$ are a series arrangement of two capacitors $C_2$, a series arrangement of two resistors $R_2$, and a capacitor The midpoints of the $R_2$-$R_2$ and $C_2$-$C_2$ series arrangements are connected together and further connected to the non-inverting input of op-amp 20.

FETs $M_6$ and $M_7$ have their drains also connected to nodes $N_3$ and $N_4$, respectively. The sources of FETs $M_6$ and $M_7$ are connected together and in series with the drain of FET M5, through which a current $I_2$ flows. The FETs $M_6$ and $M_7$ are amplifier stages whose gate electrodes are connected to receive input voltages, $V_{i1}$ and $V_{i2}$, respectively. The source of FET M5 is connected to $V_{ss}$.

For optimum operation of the differential amplifier 16, the aspect ratios of the various FETs (i.e., the ratio of channel width, W, to channel length, L) should satisfy the following relationships, where each indicium corresponds to that assigned to the respective FET in FIG. 3:

$(W/L)_1 > (W/L)_2$;

$(W/L)_5 > (W/L)_3$;

$(W/L)_3 = (W/L)_4$;

$(W/L)_6 = (W/L)_7$;

and $(W/L)_8 = (W/L)_9$.

The operation of the differential amplifier 16 has the following features:

The forward voltage drop of diode $D_1$ provides a substantially constant voltage, $V_B \cong -0.5$ V. Due to the feedback associated with the op-amp 20, both the inverting and the non-inverting inputs of op-amp 20 remain at a constant DC level, $V_B \cong -0.5$ volt.

Each of the FETs $M_1$ and $M_2$ act as a diode-connected transistor having a voltage drop of $V_{GS1}$ and $V_{GS2}$, respectively. The FETs $M_3$ and $M_4$ are configured as current sources. The drains of the FETs $M_3$ and $M_4$ are forced to equal voltages, due to their connection to respective inputs of the op-amp 21. Because the aspect ratios of the FETs $M_3$ and $M_4$ are equal, an identical current $I_1$ flows into each of the FETs $M_1$, $M_2$, $M_3$ and $M_4$, and also through the resistor $R_1$.

Thus, the voltage loop equation around the loop defined by the nodes $N_1$, $N_2$ and B is:

$$I_1 R_1 + V_{GS1} = V_{GS2}$$

where $V_{GSn}$ = the gate-source voltage of the respective FET.

Because the W/L ratio of the FET $M_1$ is greater than the W/L ratio of the FET $M_2$, the gate-to-source voltage of the FET $M_1$, $V_{GS1}$, will be smaller than the gate-to-source voltage of the FET $M_2$, $V_{GS2}$.

Assuming that the FETs $M_1$ and $M_2$ operate in the weak inversion (subthreshold) region, and their drain-to-source voltage $V_{DS} > 3$ (kT/q) (i.e., the saturation region), then their gate-to-source voltages can be approximated as:

$$V_{GS} \cong n \left( \frac{kT}{q} \right) \ln \left[ \frac{I}{I_{DO} \left( \frac{W}{L} \right)} \right]$$

where $I_{DO}$ is the characteristic current which is process dependent.

Substituting for the gate-to-source voltages and solving for the current $I_1$ results in:

$$I_1 = n \left( \frac{kT}{q} \right) \left( \frac{1}{R_1} \right) \ln \left[ \frac{\left( \frac{W}{L} \right)_1}{\left( \frac{W}{L} \right)_2} \right]$$

where n = the weak-inversion slope factor, which is highly process dependent and has a value of between 1.1 and 1.9;

kT/q = thermal voltage which is highly temperature dependent and is approximately equal to 26 mV at room temperature; and $R_1$ is the absolute resistance value of resistor $R_1$, which is highly process and temperature dependent.

The current, $I_2$, flowing through the FET M5 is mirrored over from the FETs $M_3$ and $M_4$. That is, the value of the current $I_2$ is based on $I_1$ and the ratio of the aspect ratios of the FETs M5 and $M_3$, or $(W/L)_5$ and $(W/L)_3$, respectively. Thus, $I_2$ is as follows:

$$I_2 = \frac{\left( \frac{W}{L} \right)_5}{\left( \frac{W}{L} \right)_3} I_1 =$$

$$\frac{\left( \frac{W}{L} \right)_5}{\left( \frac{W}{L} \right)_3} \cdot n \left( \frac{kT}{q} \right) \left( \frac{1}{R_1} \right) \ln \left[ \frac{\left( \frac{W}{L} \right)_1}{\left( \frac{W}{L} \right)_2} \right]$$

For simplicity, the differential amplifier 16, shown in FIG. 3, has a constant gain, that is, the current source formed by the FET M5 is a constant current source. However, if the differential amplifier 16 is to have a programmable gain, the current source M5 would be replaced by a programmable current source, using conventional techniques.

Because of the feedback, the voltage which appears on the inverting input of op-amp 20 also appears at the non-inverting input of op-amp 20, which, in turn, biases the midpoint of the $R_2$-$R_2$ and $C_2$-$C_2$ network. This enables low amplitude AC signals (e.g., P-waves and R-waves) across the inputs $V_{i1}$ and $V_{i2}$ to be amplified about this $V_B \cong -0.5$ volts. Thus, the currents produced by the current sources formed by the FETs $M_8$ and $M_9$ are adjusted by the op-amp 20 to maintain the average voltage of signals $V_{o1}$ and $V_{o2}$ at the voltage $V_B$ appearing at node B. Since the inverting and non-inverting inputs of op-amp 20 remain at a constant DC level, $V_B \cong -0.5$ volt, the op-amp 20 forces the DC common mode voltage of the output signals $V_{o1}$ and $V_{o2}$ to be constant and independent of variable input common mode signals. Thus, the large common mode signals resulting from the generation of stimulation pulses are significantly reduced in the front-end amplifier.

The purpose of the capacitors $C_1$ and $C_2$ in the differential amplifier 16 is to bandlimit the frequency response of the differential amplifier 16 to the significant frequency components of the P-waves and the R-waves, which are below 200 Hz. The dominant pole of the amplifier is determined by:

$$f_p = \frac{1}{2\pi} \cdot \frac{1}{R_2(C_2 + 2C_1)}$$

The gain of the differential amplifier 16 is determined by:

$$A_1 = \frac{V_{o2} - V_{o1}}{V_{i2} - V_{i1}} = g_{M6} R_2 = g_{M7} R_2 = (R_2) \cdot \left[ \frac{\left( \frac{I_2}{2} \right)}{\left( n \left( \frac{kT}{q} \right) \right)} \right]$$

where $g_{M6}$ and $g_{M7}$ are the transconductance of the FETs $M_6$ and $M_7$, respectively.

Substituting in for $I_2$, reduces to:

$$A_1 = \text{gain} = \frac{1}{2}\left(\frac{R_2}{R_1}\right)\frac{\left(\frac{W}{L}\right)_5}{\left(\frac{W}{L}\right)_3}\ln\left[\frac{\left(\frac{W}{L}\right)_1}{\left(\frac{W}{L}\right)_2}\right]$$

It can be seen from the equation for the gain $A_1$ that it does not depend on n, the individual values of $R_1$ and $R_2$, or temperature. It only depends on the ratio of $R_2$ to $R_1$ and the aspect ratios of the associated FETs. Therefore, the accuracy of the amplification produced by the differential amplifier 16 will be within 1 to 2% when circuit 16 is fabricated according to integrated circuit technology.

It can also be seen from the equation for the gain $A_1$ that the aspect ratios of the FETs $M_1$ and $M_2$ contribute to the gain as a function of the natural logrithmic scale. Thus, $M_1$ should be selected to be several factors larger than $M_2$, however, very large factors do not make a significant difference when taking the natural log thereof, and further would require a considerable amount of real estate on the chip substrate. In the preferred embodiment, to produce a gain $A_1$ equal to 10, the FET $M_1$ is a factor of 2.7 times larger than the FET $M_2$ (i.e., ln (2.7)≅1); $R_2$ is 2 times larger than $R_1$; and the FET $M_5$ is 10 times larger than the FET $M_3$ to produce a gain $A_1=10$. These values are only exemplary and are included for purposes of illustrating one embodiment of the present invention.

The selection of the values for the resistors $R_1$ and $R_2$ will determine not only the gain of the differential amplifier 16, but the current consumption, and further are limited by real estate and processing constraints. In the preferred embodiment, the resistor $R_2$ is 5 MΩ and $R_1$ is 2.5 MΩ. However, the current consumption could be made lower by giving the resistor $R_1$ a high resistance value, e.g., 5 MΩ. However, the fabrication of resistors having a value substantially greater than 5 MΩ for $R_2$, using current IC technology, requires an unacceptably large real estate area, or specialized and expensive processing.

The capacitors $C_1$ and $C_2$ are on-chip capacitors and are thus kept relatively small. For example, to achieve a $f_p$ of approximately 220 Hz, $C_1=70$ pF and $C_2=4$ pF.

Consequently, the differential amplifier 16 is capable of amplifying low level signals with a very high S/N ratio. The current consumption by such an amplifier is dependent essentially on the amplifier gain. According to the present invention, the differential amplifier 16 is given a gain which is substantially lower than the gain which would be required if the entire amplification operation were to be performed by that amplifier. By way of example, while amplification of input voltages might require a total gain on the order of 100, in accordance with the present invention, the differential amplifier 16 can be configured to have a gain on the order of 10. Then, if suitable component values are selected, the total current drain will be 200 nA, which is an acceptable value.

Because the operation of the differential amplifier 16 does not involve any switching, the amplifier is free from switching noise, so that low level signal inputs are not corrupted by such switching.

Upon the appearance of the leading edge of a stimulation pulse from the pulse generator 14, conventional switching circuitry (not shown) within the pacemaker 1 decouples the inputs of the sensing module 4 from the electrodes and connect those inputs to a low impedance DC input voltage (not shown), so that those inputs are never floating. At a selected time after the stimulation pulse trailing edge, the inputs of the sensing module 4 are reconnected to receive signals corresponding to those on the electrodes. The circuitry and controls for performing these functions are conventional in the art and do not, per se, constitute novel features of the present invention.

Thus, the current consumption in the differential amplifier 16 is reduced to an acceptable level by giving the differential amplifier 16 a suitably low gain. Then, in order to give the front-end amplifier 19 (FIG. 2) the desired overall gain level, the output of the differential amplifier 16 is connected, according to the present invention, to the switched-capacitor amplifier 18. By giving the differential amplifier 16 a gain on the order of 10, the input signals to the switched-capacitor amplifier 18 becomes large enough that noise due to capacitor switching will not corrupt the resultant output signal to an unacceptable extent. Any errors introduced by the switched-capacitor amplifier 18 into the signal being amplified will (compared to prior art systems employing only a switched-capacitor amplifier) be reduced by a factor corresponding to the gain of the differential amplifier 16; i.e., in the specific example described above will be divided by a factor on the order of 10.

In FIG. 4, a preferred embodiment of the second stage for the front-end amplifier 19 is shown as a switched-capacitor amplifier 18, to which the invention is not limited. The switched-capacitor amplifier 18 includes an op-amp 24 with a first switched-capacitor circuit 26 having terminals 23 and 25, and a second switched-capacitor circuit 28 having terminals 27 and 29. The terminals 23 and 27 of switched-capacitor circuits 26, 28 are coupled to the outputs of the differential amplifier 16 (FIG. 3), $V_{o1}$ and $V_{o2}$, respectively. The terminals 25 and 29 of switched-capacitor circuits 26, 28 are coupled to the inverting and non-inverting inputs of op-amp 24, respectively.

The switched-capacitor amplifier 18 also has a third switched-capacitor circuit 32 having terminals 31 and 33. The terminal 33 of switched-capacitor circuit 32 is connected to the output, $V_{out}$, and the terminal 31 is connected to the inverting input of the op-amp 24.

A fourth switched-capacitor circuit 34 has terminals 35 and 37. The terminal 35 of the switched-capacitor circuit 34 is coupled to the noninverting input of op-amp 24 and the terminal 37 is connected to a DC reference voltage $V_{dc}=-0.5$ volts.

A first filter capacitor $C_{T1}$ is connected between the output, $V_{out}$, and the inverting input of the op-amp 24. A second filter capacitor $C_{T2}$ is connected between the non-inverting input of the op-amp 24 and ground ($V_{DD}$). The purpose of capacitors $C_{T1}$ and $C_{T2}$ is to band-limit the frequency response of the switched-capacitor amplifier 18 to the significant frequency components of P-waves and R-waves, which are less than 200 Hz. That is, a switched-capacitor circuit 32 (or 34) acts like a resistor in parallel with $C_{T1}$ (or $C_{T2}$) to form a low pass filter.

Figure 5:
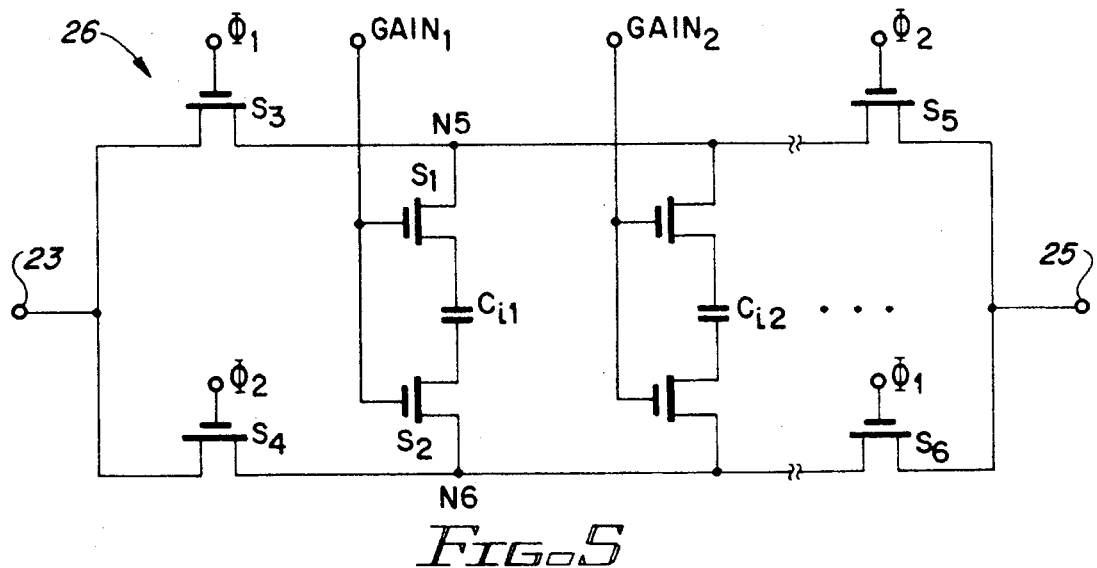
FIG. 5 is a circuit diagram of a switched-capacitor circuitry which appears at the inputs of the switched-capacitor amplifier.
Figure 6:
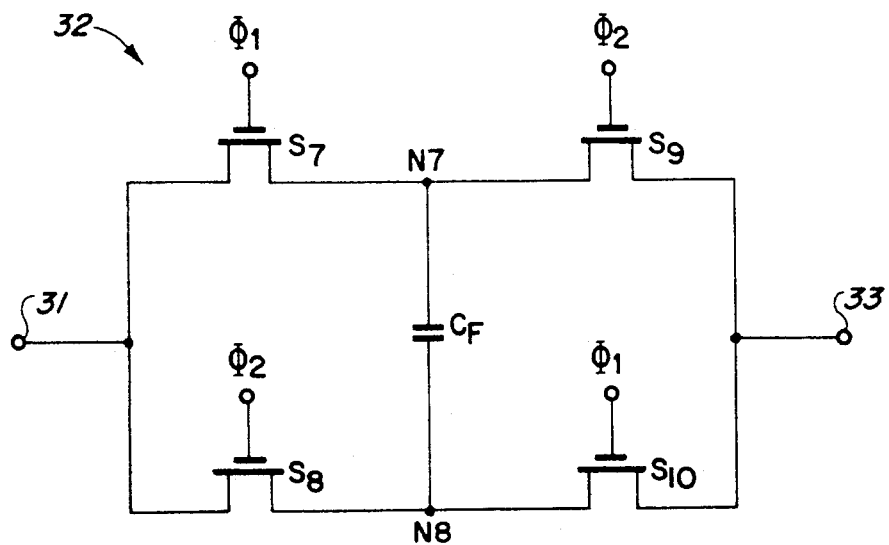
FIG. 6 is a circuit diagram of a switched-capacitor circuitry which appears in the feedback paths of the switched-capacitor amplifier.

The switched-capacitor circuit 26, which is described in FIG. 5, is identical in construction and component values to the switched-capacitor circuit 28. Thus, only the switched-capacitor circuit 26 will be described in detail in FIG. 5. Likewise, the switched-capacitor circuit 32, which is described in FIG. 6, is identical in construction and component values to the switched-capacitor circuit 34. Thus, only the switched-capacitor circuit 32 will be described in detail in FIG. 6. The capacitors, $C_{T1}$ and $C_{T2}$, also have identical values. As such, it should be apparent that the op-amp 24 is configured as a balanced differential amplifier.

As shown in FIG. 5, the switched-capacitor circuit 26 is composed of at least one capacitor $C_i$ (for fixed gain) and preferably a plurality of capacitors $C_{i1}, C_{i2} \ldots C_{in}$ (for programmable gains), where n corresponds to the number of programmable gains. Each of the plurality capacitors $C_{in}$ are coupled across nodes N5 and $N_6$ by FET switches (e.g., $C_{i1}$ is coupled to N5 and $N_6$ by switches $S_1$ and $S_2$, respectively, when gain1 is selected, etc.). Each of these capacitors $C_{in}$ has a respectively different capacitance value. Only a selected one of the capacitors $C_{in}$ in each switched-capacitor circuit 26, 28 will be selected for operative connection in the switched-capacitor amplifier 18 under the control of gain selection signals which are supplied from control system 2 (FIG. 1). In each of the switched-capacitor circuits 26 and 28, there can be provided any desired number of capacitors, as indicated in FIG. 5, with each capacitor being associated with respective switching FETs connected to a respectively different gain selection line. Thus, the gain of the switched-capacitor amplifier 18 can be easily altered.

The terminal 23 of switched-capacitor circuit 26 is connected to one side of a pair of FET switches $S_3$ and $S_4$. The other side of the FET switches $S_3$ and $S_4$ are connected to a respective one of nodes, $N_5$ and $N_6$, and also to one side of FET switches $S_5$ and $S_6$, respectively. The other side of the FET switches $S_5$ and $S_6$ are connected together to form the terminal 25.

The FET switches $S_3$ and $S_6$ are configured to close upon receiving a gate signal of $\phi_1$. The FET switches $S_4$ and $S_5$ are configured to close upon receiving a gate signal of $\phi_2$. In this way, the selected capacitor $C_{in}$ is switched, with a first polarity during clock signal $\phi_1$ and with a second polarity during clock signal $\phi_2$, between the output voltage, $V_{o1}$, and the inverting input of op-amp 24 (FIG. 4).

As mentioned above, switched-capacitor circuit 28 is identical to switched-capacitor circuit 26 with the exception that the output voltage $V_{o2}$ from the differential amplifier 16 is connected the terminal 27 of the switched-capacitor circuit 28 and the terminal 29 is connected to the non-inverting input of the op-amp 24. Thus, the selected capacitor $C_{in}$ of the switched-capacitor circuit 28 is switched, with a first polarity during clock signal $\phi_1$ and with a second polarity during clock signal $\phi_2$, between the output voltage, $V_{o2}$, and the non-inverting input of op-amp 24 (FIG. 4).

As shown in FIG. 6, the switched-capacitor circuit 32 is composed of a feedback capacitor $C_F$. The terminal 31 of switched-capacitor circuit 32 is coupled to a pair of FET switches $S_7$ and $S_8$. The other side of the FET switches $S_7$ and $S_8$ are connected to a respective one of nodes, $N_7$ and $N_8$, and also to one side of FET switches $S_9$ and $S_{10}$, respectively. The other side of the FET switches $S_9$ and $S_{10}$ are connected together to form the terminal 33.

The FET switches $S_7$ and $S_{10}$ are configured to close upon receiving a gate signal of $\phi_1$. The FET switches $S_8$ and $S_9$ are configured to close upon receiving a gate signal of $\phi_2$. In this way, the capacitor $C_F$ is switched, with a first polarity during clock signal $\phi_1$ and with a second polarity during clock signal $\phi_2$, between the inverting input and the output of the op-amp 24 (FIG. 4).

As mentioned above, switched-capacitor circuit 34 is identical to switched-capacitor circuit 32 with the exception that the non-inverting input of op-amp 24 (FIG. 4) is connected the terminal 35 of the switched-capacitor circuit 34 and the terminal 37 is connected to a DC voltage reference ≅0.5 volts.

As shown in FIG. 7, the non-overlapping clock pulses applied to respective switching FETs have a timing such that one set of switching FETs will be open circuited before the other set of FETs is close circuited. This assures that, during operation of the switched-capacitor amplifier 18, none of the capacitors will ever be short circuited.

Since the feedback capacitors in the switched-capacitor circuits 32 and 34 preferably each have a feedback capacitor of value $C_F$ (for a balanced differential amplifier), the gain $A_2$ of the switched-capacitor amplifier 18 is equal to the ratio of the selected $C_i$ over the capacitor $C_F$. Advantageously, the switched-capacitor amplifier 18 can be designed to have a very low current consumption at the highest desirable gain (e.g., a gain of 10). By doing this, the gain of the switched-capacitor amplifier 18 can be programmed without concern for its current consumption.

As is already known in the art, the switched-capacitor amplifier 18 performs a sampling operation on the potentials $V_{O1}$ and $V_{O2}$ when the FET switches controlled by $\phi_1$ are opened and closed in alternation with the FET switches controlled by $\phi_2$. When the switches are operated at a suitable sampling frequency, the DC gain of the switched-capacitor amplifier 18 will be essentially proportional to the ratio of the capacitance of each capacitor $C_i$ to the capacitance of the $C_F$ capacitor. Theoretically, the sampling frequency should be at least the Nyquist rate, which is two times the frequency of the highest frequency component to be amplified. However, in practice, the sampling rate should be at least five times that signal frequency and for the use contemplated by the present invention, the sampling rate may be on the order of 1 to 2 KHz.

The switched-capacitor units utilized in the switched-capacitor amplifier 18 behave as resistors having extremely large resistance values, on the order of hundreds of MΩ, thereby realizing an extremely low current consumption.

In accordance with the present invention, when the differential amplifier 16 has a gain on the order of 10, the gain of the switched-capacitor amplifier 18 can be on the order of 10, resulting in a total gain of 100 for the front-end amplifier circuit 19. Although. operation of switched-capacitor amplifier 18 adds noise to the amplified signal, due primarily to capacitor switching, the fact that the input signal to the switched-capacitor amplifier 18 is substantially higher than the incoming cardiac signals produces the result that the switching noise has a much smaller influence on the accuracy of the output signal from op-amp 24. This output signal is further processed in the sensing module 4, as described above, and is then delivered to control system 2, where it is employed in a conventional manner to control the generation or inhibiting of heart stimulation pulses.

When used in a cardiac pacemaker, the cardiac signals appearing the electrodes and which are to be amplified generally have major frequency components less than 200 Hz and a magnitude. in the range of 0.1–10 mV. The amplifier circuit according to the present invention can be constructed to create a very low level of noise in order to accurately amplify such small differential voltages. Because of the division of amplification between two amplifiers, the overall current consumption of the amplifier circuit is very low, thereby extending the useful life of the implanted battery. A circuit of the type contemplated by the present invention can be made in the form of a monolithic IC possibly integrated with other circuits of a pacemaker chip. The circuit can be constructed to have a dynamic range on the order of 40–50 dB in order to satisfactorily amplify various differential signals. The circuit according to the invention will also have a high common mode rejection to attenuate common mode signals due to stimulation pulses.

Any noise of other distortion introduced into a signal by the operation of the switched-capacitor amplifier 18 has a reduced effect on the overall signal. Compared to the use of a switched-capacitor amplifier alone, the effect of the noise introduced by the switched-capacitor amplifier on the cardiac signals originating on the electrodes, in a circuit according to the present invention, will be reduced by a factor corresponding to the gain of the differential amplifier 16.

In addition, when the differential amplifier 16 is constructed in fully differential form, common mode rejection of the entire circuit is improved.

By constructing the switched-capacitor amplifier 18 to have a balanced input configuration at the inverting and noninverting inputs of op-amp 24, charge injection noise will be minimized, resulting in more accurate amplification.

Thus, the present invention represents a form of hybrid approach, employing a linear, differential amplifier stage as an first stage and a switched-capacitor amplifier stage as the second stage. With this arrangement, the gain of the linear, differential amplifier can be reduced, thereby reducing current consumption. The switched-capacitor amplifier can be made to have a low current consumption for an appropriate gain level and since the switched-capacitor amplifier receives a higher amplitude input signal, the effect of switching noise on the overall quality of the amplified signal will be significantly reduced. In practical embodiments of the type described above, where amplifiers 16 and 18 can each have a gain of 10, the current consumption in those amplifiers can be held to about 200 nA.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An implantable stimulation device, the stimulation device having pulse generating means for generating stimulation pulses, sensing means for sensing cardiac signals, and control means for controlling the pulse generating means to generate stimulation pulses to a heart in the absence of cardiac depolarizations, and for inhibiting the pulse generating means in the presence of cardiac depolarizations, the sensing means comprising:

linear amplifying means, having a first gain associated therewith, for amplifying the cardiac signals, the linear amplifying means having input means for receiving the cardiac signals, the linear amplifying means further having output means for producing a first output signal;

a switched-capacitor amplifier, having a second gain associated therewith, for amplifying the first output signal of the linear amplifying means, the switched-capacitor amplifier having input means for receiving the first output signal, the switched-capacitor amplifier further having an output for producing a second output signal having a noise content produced substantially entirely in the switched-capacitor amplifier; and threshold detecting means for detecting when the second output signal exceeds a prescribed threshold corresponding to an occurrence of a cardiac depolarization.

2. The implantable stimulation device, as recited in claim 1, wherein:

the linear amplifying means has a first current drain proportional to the first gain, the first gain having a low gain value;

the switched-capacitor amplifier has a second current drain having low current consumption at the second gain;

the sensing means has an overall gain which is the product of the first and the second gains and an overall current consumption which is the sum of the first and the second current drains;

whereby the overall gain is sufficiently high enough to amplify cardiac signals and the overall current consumption is kept low so that longevity of the implantable stimulation device is extended.

3. The implantable stimulation device, as recited in claim 1, wherein:

the input means of the linear amplifying means is a differential input.

4. The implantable stimulation device, as recited in claim 3, wherein:

the output means of the linear amplifying means is a differential output; and the input means of the switched-capacitor amplifier is a balanced differential input.

5. The implantable stimulation device, as recited in claim 1, wherein the first gain of the linear amplifying means comprises a low amplitude fixed gain.

6. The implantable stimulation device, as recited in claim 5, wherein the fixed gain of the linear amplifying means comprises a gain of 20 or less.

7. The implantable stimulation device, as recited in claim 1, wherein the first gain of the linear amplifying means comprises a low amplitude programmable gain.

8. The implantable stimulation device, as recited in claim 1, wherein the gain of the switched-capacitor amplifier comprises a programmable gain.

9. The implantable stimulation device, as recited in claim 1, wherein:

the sensing means has an overall gain which is the product of the first gain and the second gain.

10. The implantable stimulation device, as recited in claim 9, wherein:

the overall gain of the sensing means is programmable from 1 to 100.

11. The implantable stimulation device, as recited in claim 1, wherein the linear amplifying means includes an input stage comprising:

power source means for providing a positive and a negative voltage, the positive voltage corresponding to ground;

a reference voltage means, coupled to the positive voltage, for producing a negative DC reference voltage, $V_B$;

a first operational amplifier, powered by the power source means, having an inverting input, a non-inverting input and an output;

a resistor, $R_1$, coupled at a first end to the reference voltage means;

a first diode-connected FET transistor, $M_1$, having a drain connected to a second end of the resistor $R_1$ and a source connected to the non-inverting input of the first operational amplifier;

a first current source FET transistor, $M_3$, connected in series between the non-inverting input of the first operational amplifier and the negative voltage, the output of the first operational amplifier controlling a gate of the first current source;

a second diode-connected FET transistor, $M_2$, having a drain connected to the first end of the resistor $R_1$ and a source connected to the inverting input of the first operational amplifier;

a second current source FET transistor, $M_4$, connected in series between the inverting input of the first operational amplifier and the negative voltage, the output of the first operational amplifier controlling a gate of the second current source;

wherein the first and second current source FET transistors each produce a current $I_1$ therethrough, the current $I_1$ also flowing through the resistor $R_1$.

12. The implantable stimulation device, as recited in claim 11, wherein the first and second current source FET transistors each have predetermined width, W, length, L, and a respective aspect ratio defined as $(W/L)_i$, where i corresponds to the respective FET transistor, the current $I_1$ produced by the first and second current sources being defined by the equation:

$$I_1 = n\left(\frac{kT}{q}\right)\left(\frac{1}{R_1}\right) \ln\left[\frac{\left(\frac{W}{L}\right)_1}{\left(\frac{W}{L}\right)_2}\right]$$

n=the weak-inversion slope factor, which is highly process dependent;

kT/q=thermal voltage, which is highly temperature dependent; and $R_1$ is the absolute resistance value of resistor $R_1$, which is highly process and temperature dependent.

13. The implantable stimulation device, as recited in claim 12, further comprising a current mirror FET transistor, $M_5$, having an aspect ratio $(W/L)_5$ which provides a current $I_2$ related to the current $I_1$ as defined by the equation:

$$I_2 = \frac{\left(\frac{W}{L}\right)_5}{\left(\frac{W}{L}\right)_3} I_1 = \frac{\left(\frac{W}{L}\right)_5}{\left(\frac{W}{L}\right)_3} \cdot n\left(\frac{kT}{q}\right)\left(\frac{1}{R_1}\right) \ln\left[\frac{\left(\frac{W}{L}\right)_1}{\left(\frac{W}{L}\right)_2}\right].$$

14. The implantable stimulation device, as recited in claim 13, wherein the linear amplifying means includes an amplification stage having differential outputs, $V_{o1}$ and $V_{o2}$, comprising:

two resistors having a value $R_2$ and connected in series across the differential output;

a second operational amplifier having an output, an inverting input coupled to the negative DC reference voltage, $V_B$, and a non-inverting input coupled between the series resistors;

third and fourth current source FET transistors, $M_8$ and $M_9$, respectively, each having a source connected to the positive voltage, a drain connected to a respective one of the differential outputs, $V_{o1}$ and $V_{o2}$, respectively, and a gate coupled to the output of the second operational amplifier;

first and second amplifying FET transistors, $M_6$ and $M_7$, having a respective drain connected to the differential outputs, $V_{o1}$ and $V_{o2}$, respectively, their sources connected to a drain of the current mirror FET transistor, $M_5$, and a gate which acts as one input of the sensing means;

wherein the first gain of the linear amplifying means is defined by the equation:

$$A_1 = \text{gain} = -\frac{1}{2}\left(\frac{R_2}{R_1}\right) \frac{\left(\frac{W}{L}\right)_5}{\left(\frac{W}{L}\right)_3} \ln\left[\frac{\left(\frac{W}{L}\right)_1}{\left(\frac{W}{L}\right)_2}\right]$$

whereby the gain, $A_1$, is independent of the process dependent variables n, kT/q and the absolute resistance values of resistors $R_1$ and $R_2$.

15. An implantable stimulation device, the stimulation device having pulse generating means for generating stimulation pulses, sensing means for sensing cardiac signals, and control means for controlling the pulse generating means to generate stimulation pulses to a heart in the absence of cardiac depolarizations, and for inhibiting the pulse generating means in the presence of cardiac depolarizations, the sensing means comprising:

first amplifying means, having a first gain associated therewith, for linearly amplifying the cardiac signals, the first amplifying means having input means for receiving the cardiac signals, the first amplifying means further having output means for producing a first output signal, the first amplifying means has a current consumption proportional to the first gain;

second amplifying means, having a second gain associated therewith, for switch-capacitively amplifying the first output signal of the first amplifying means, the second amplifying means having input means for receiving the first output signal, the second amplifying means further having an output for producing a second output signal, the second amplifying means having a low current consumption at the second gain; and threshold detecting means for detecting when the second output signal exceeds a prescribed threshold corresponding to an occurrence of a cardiac depolarization;

whereby the overall current consumption is kept low so that longevity of the implantable stimulation device is extended.

16. The implantable stimulation device, as recited in claim 15, wherein:

the first amplifying means comprises a linear operational amplifier; and the input means of the linear operational amplifier is a differential input.

17. The implantable stimulation device, as recited in claim 15, wherein the second amplifying means comprises a switched-capacitor amplifier.

18. The implantable stimulation device, as recited in claim 15, wherein the first gain of the first amplifying means comprises a low amplitude fixed gain.

19. The implantable stimulation device, as recited in claim 15, wherein the gain of the second amplifying means comprises a programmable gain.

20. The implantable stimulation device, as recited in claim 15, wherein the first gain of the first amplifying means comprises a low amplitude programmable gain.

21. An implantable stimulation device, the stimulation device having pulse generating means for generating stimulation pulses, sensing means for sensing cardiac signals, and control means for controlling the pulse generating means to generate stimulation pulses to a heart in the absence of cardiac depolarizations, and for inhibiting the pulse generating means in the presence of cardiac depolarizations, the sensing means comprising:

linear amplifying means, having a low gain value and low noise content associated therewith, for amplifying the cardiac signals and for producing a first output signal thereof, the linear amplifying means having a first, low current drain proportional to the low gain value;

a switched-capacitor amplifier, having a second gain associated therewith, for amplifying the first output signal of the linear amplifying means and for producing a second output signal thereof, the switched-capacitor amplifier having a noise component due to switches associated with the switched-capacitor amplifier, the switched-capacitor amplifier having a second, low current drain at the second gain; and threshold detecting means for detecting when the second output signal exceeds a prescribed threshold corresponding to an occurrence of a cardiac depolarization;

whereby the sensing means has a total noise content that is produced substantially entirely by the switched-capacitor amplifier, a total gain which is the product of the first and the second gains, and a total current consumption which is the sum of the first and the second current drains, so as to produce a low noise, low power, high gain amplifier suitable for sensing cardiac signals without unnecessarily depleting battery capacity of the implantable stimulation device.

22. The implantable stimulation device, as recited in claim 21, wherein the gain of the switched-capacitor amplifier means comprises a programmable gain, so as to produce a low noise, low power, programmable gain amplifier.

* * * * *